United States Patent
McDonald, II

(10) Patent No.: US 10,898,189 B2
(45) Date of Patent: Jan. 26, 2021

(54) PUSH-PULL STAPLER WITH TWO DEGREE OF FREEDOM WRIST

(71) Applicant: Intuitive Surgical Operations, Inc., Sunnyvale, CA (US)

(72) Inventor: William A. McDonald, II, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 249 days.

(21) Appl. No.: 15/772,530

(22) PCT Filed: Oct. 31, 2016

(86) PCT No.: PCT/US2016/059649
§ 371 (c)(1),
(2) Date: Apr. 30, 2018

(87) PCT Pub. No.: WO2017/083130
PCT Pub. Date: May 18, 2017

(65) Prior Publication Data
US 2018/0317915 A1     Nov. 8, 2018

Related U.S. Application Data

(60) Provisional application No. 62/255,150, filed on Nov. 13, 2015.

(51) Int. Cl.
*A61B 17/072*     (2006.01)
*A61B 17/29*      (2006.01)
(Continued)

(52) U.S. Cl.
CPC ........ *A61B 17/07207* (2013.01); *A61B 17/29* (2013.01); *A61B 34/37* (2016.02);
(Continued)

(58) Field of Classification Search
CPC ... A61B 17/07207; A61B 17/29; A61B 34/37; A61B 2017/07214; A61B 2017/0069;
(Continued)

(56) References Cited

U.S. PATENT DOCUMENTS 5,433,721 A * 7/1995 Hooven ............... A61B 17/068
                                                    227/175.1
5,522,830 A     6/1996 Aranyi
(Continued)

FOREIGN PATENT DOCUMENTS

EP     0484672 A2     5/1992
EP     2522280 A1     11/2012

OTHER PUBLICATIONS

International Search Report and Written Opinion for Application No. PCT/US2016/059649, dated Feb. 16, 2017, 11 pages (ISRG07380/PCT).

(Continued)

*Primary Examiner* — Thanh K Truong
*Assistant Examiner* — Scott A Howell
(74) *Attorney, Agent, or Firm* — Schwegman Lundberg & Woessner, P.A.

(57) ABSTRACT

A surgical instrument is provided comprising: a first jaw having a distal end and a proximal end wherein the proximal end of the first jaw is attached to a lever arm that includes a levering cam slot having a proximal portion and a distal portion; a second jaw having a distal end and a proximal end wherein the proximal end of the second jaw is secured to a base that includes a linear cam slot aligned with a longitudinal axis of the second jaw axis and having a proximal portion and a distal portion; a pivot rotatably mounting the first jaw to the second jaw, wherein a pivot axis extends between the first jaw and the lever arm; a cam pin configured to extend through and engage the levering cam slot and the (Continued)

linear cam slot; a linear drive member operatively coupled to drive the cam pin to follow the linear cam slot; wherein the cam pin imparts a lever force upon the lever arm that rotates the first jaw way from the second jaw when the cam pin contacts the distal portion of the levering cam slot and wherein the cam pin imparts a lever force upon the lever arm that rotates the first jaw toward the second jaw when the cam pin contacts the proximal end portion of the levering cam slot.

17 Claims, 13 Drawing Sheets

(51) Int. Cl.
    *A61B 17/00*         (2006.01)
    *A61B 34/37*         (2016.01)

(52) U.S. Cl.
    CPC .............. *A61B 2017/0069* (2013.01); *A61B 2017/07214* (2013.01); *A61B 2017/07257* (2013.01); *A61B 2017/2903* (2013.01); *A61B 2017/2927* (2013.01); *A61B 2017/2936* (2013.01)

(58) Field of Classification Search
    CPC .. A61B 2017/04257; A61B 2017/2903; A61B 2017/2927; A61B 2017/2936
    USPC ...................................................... 227/157.1
    See application file for complete search history.

(56) References Cited

U.S. PATENT DOCUMENTS

| | | | |
|---|---|---|---|
| 8,403,197 | B2 | 3/2013 | Vidal et al. |
| 9,168,050 | B1 * | 10/2015 | Peine ................. A61B 17/2816 |
| 9,498,242 | B2 * | 11/2016 | Crews ................... A61B 17/29 |
| 9,566,081 | B2 * | 2/2017 | Stefan ................ A61B 17/2909 |
| 2006/0020287 | A1 * | 1/2006 | Lee ...................... A61B 17/062 606/205 |
| 2011/0230910 | A1 * | 9/2011 | Stopek .................. A61B 17/29 606/205 |
| 2012/0022584 | A1 | 1/2012 | Donnigan et al. |
| 2012/0181322 | A1 | 7/2012 | Whitman et al. |
| 2013/0066318 | A1 | 3/2013 | Kerr |
| 2013/0240604 | A1 | 9/2013 | Knodel |
| 2014/0012290 | A1 | 1/2014 | Cooper et al. |
| 2014/0343550 | A1 | 11/2014 | Faller et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Extended European Search Report for Application No. 16864783.2 dated Jun. 5, 2019, 9 pages.

* cited by examiner

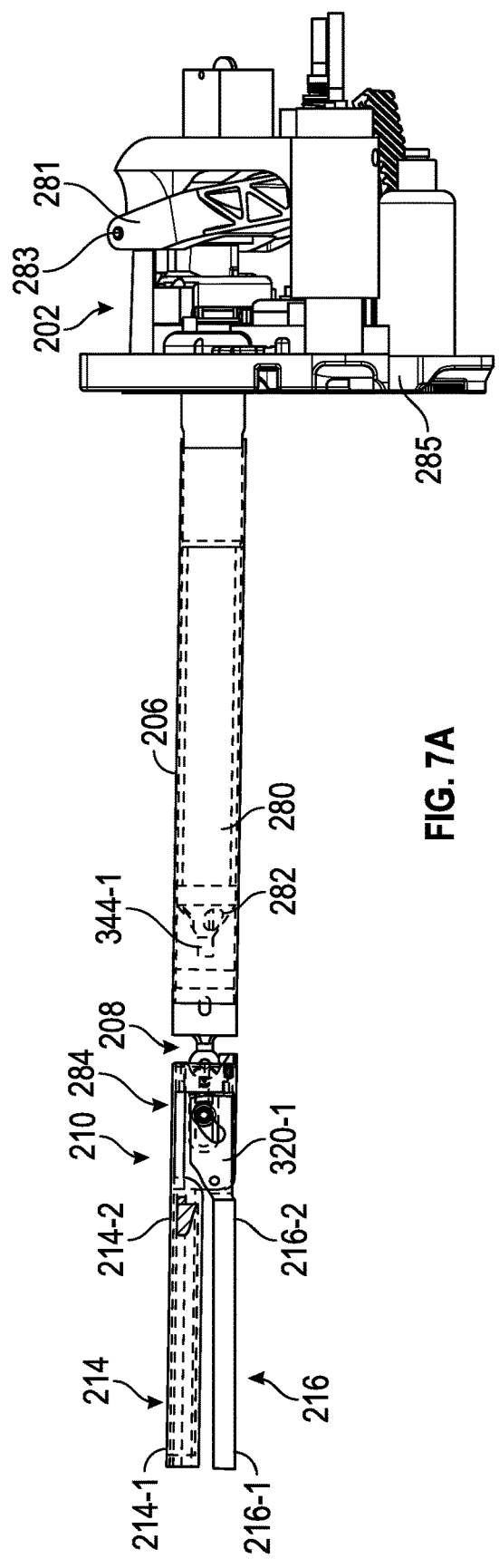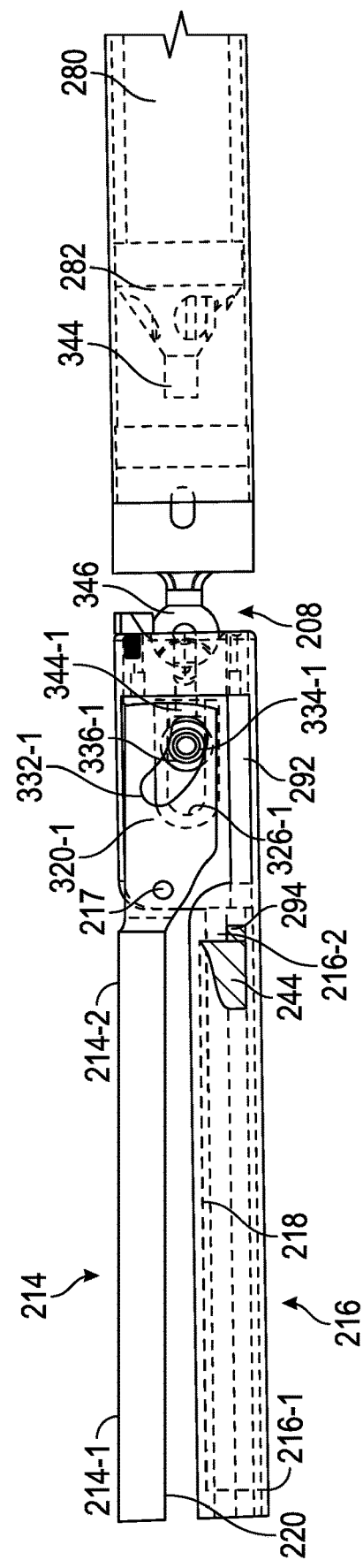
FIG. 7A
FIG. 7B

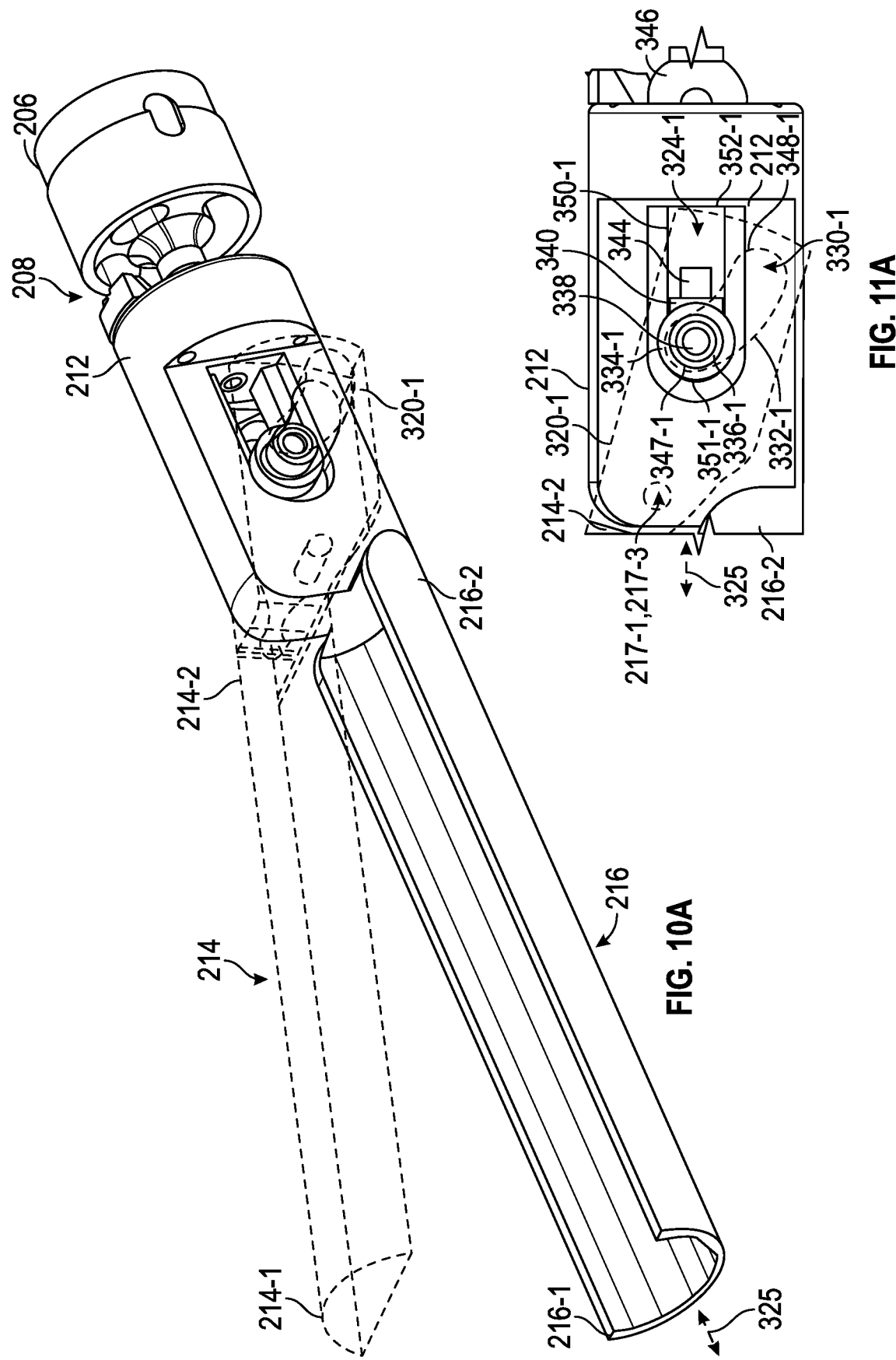

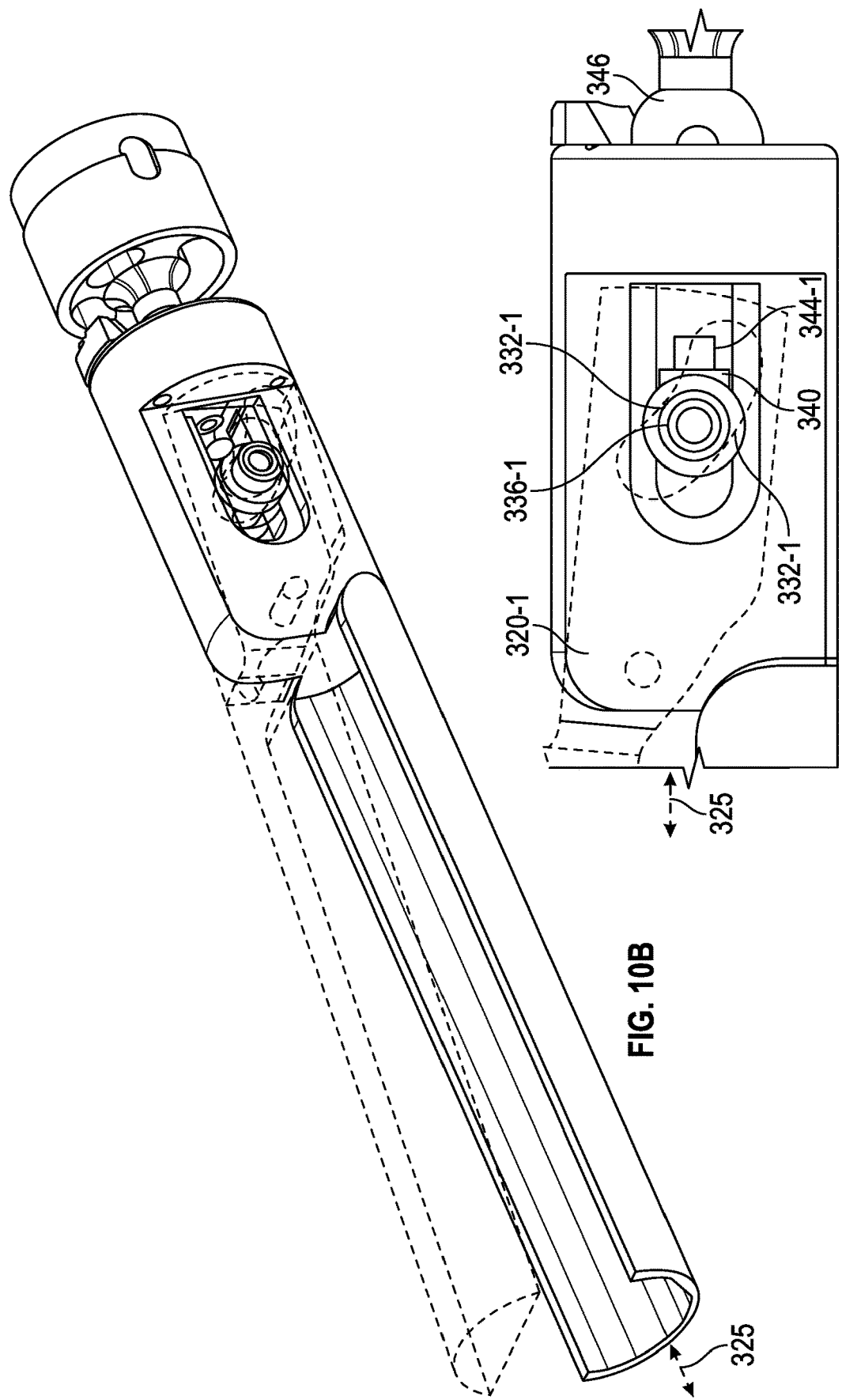

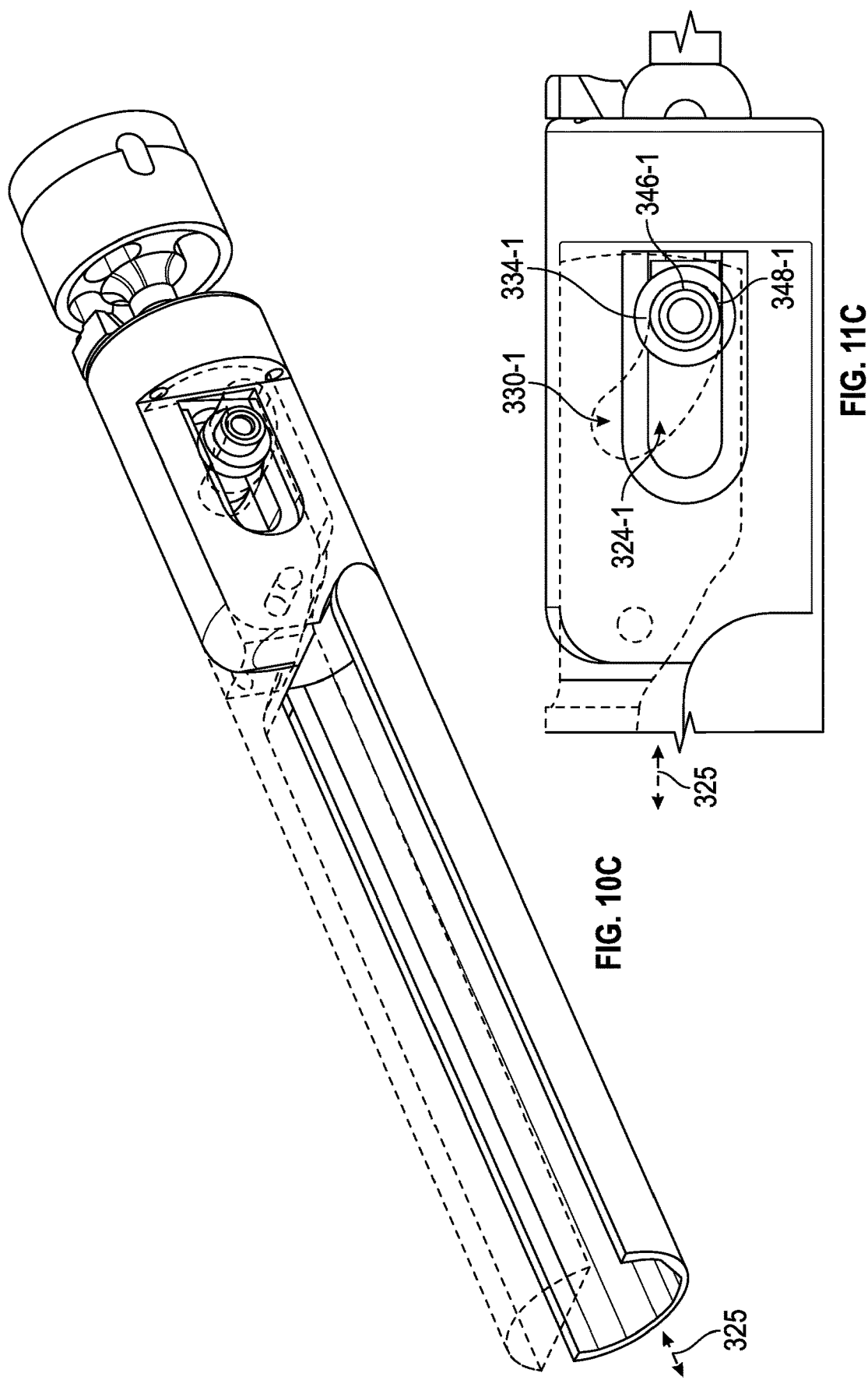

PUSH-PULL STAPLER WITH TWO DEGREE OF FREEDOM WRIST

RELATED APPLICATIONS

This patent application is a U.S. National Stage Filing under 35 U.S.C. 371 from International Application No. PCT/US2016/059649, filed on Oct. 31, 2016, and published as WO 2017/083130 A1 on May 18, 2017, which claims priority to and the benefit of the filing date of U.S. Provisional Patent Application 62/255,150, entitled "PUSH-PULL STAPLER WITH Two DEGREE OF FREEDOM WRIST" filed Nov. 13, 2015, each of which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

In one aspect, a surgical instrument includes a first jaw having a distal end and a proximal end, wherein the proximal end of the first jaw is attached to a lever arm that includes a levering cam slot having a proximal portion and a distal portion. A second jaw has a distal end and a proximal end, wherein the proximal end of the second jaw is secured to a base that includes a linear cam slot aligned with a longitudinal axis of the second jaw axis and having a proximal portion and a distal portion. A pivot rotatably mounts the first jaw to the second jaw. A pivot axis extends between the first jaw and the lever arm. A cam pin is configured to extend through and engage the levering cam slot and the linear cam slot. A linear drive member is operatively coupled to drive the cam pin to follow the linear cam slot. The distal portion of the levering cam slot is disposed such that the cam pin imparts a lever force upon the lever arm that rotates the first jaw away from the second jaw when the cam pin contacts the distal portion of the levering cam slot. The proximal portion of the levering cam slot is disposed such that the cam pin imparts a lever force upon the lever arm that rotates the first jaw toward the second jaw when the cam pin contacts the proximal end portion of the levering cam slot.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 7A is an illustrative partially transparent side view of a surgical tool assembly in accordance with some embodiments.

FIG. 7B is an illustrative partially transparent side view of the distal portion of the surgical tool assembly of FIG. 7A, enlarged to show additional details in accordance with some embodiments.

FIGS. 10A-10C are illustrative partially transparent upper-side perspective views of the jaws and base portions of an end effector in accordance with some embodiments in open (FIG. 10A), partially closed (FIG. 10B) and closed (FIG. 10C) positions in accordance with some embodiments.

FIGS. 11A-11C are enlarged side views of the first cam follower slot and the first roller cam disposed therein abutting a cam follower distal edge (FIG. 11A), abutting cam follower side edges (FIG. 11B) and abutting a cam follower proximal edge (FIG. 11C) in accordance with some embodiments.

Figure 1:
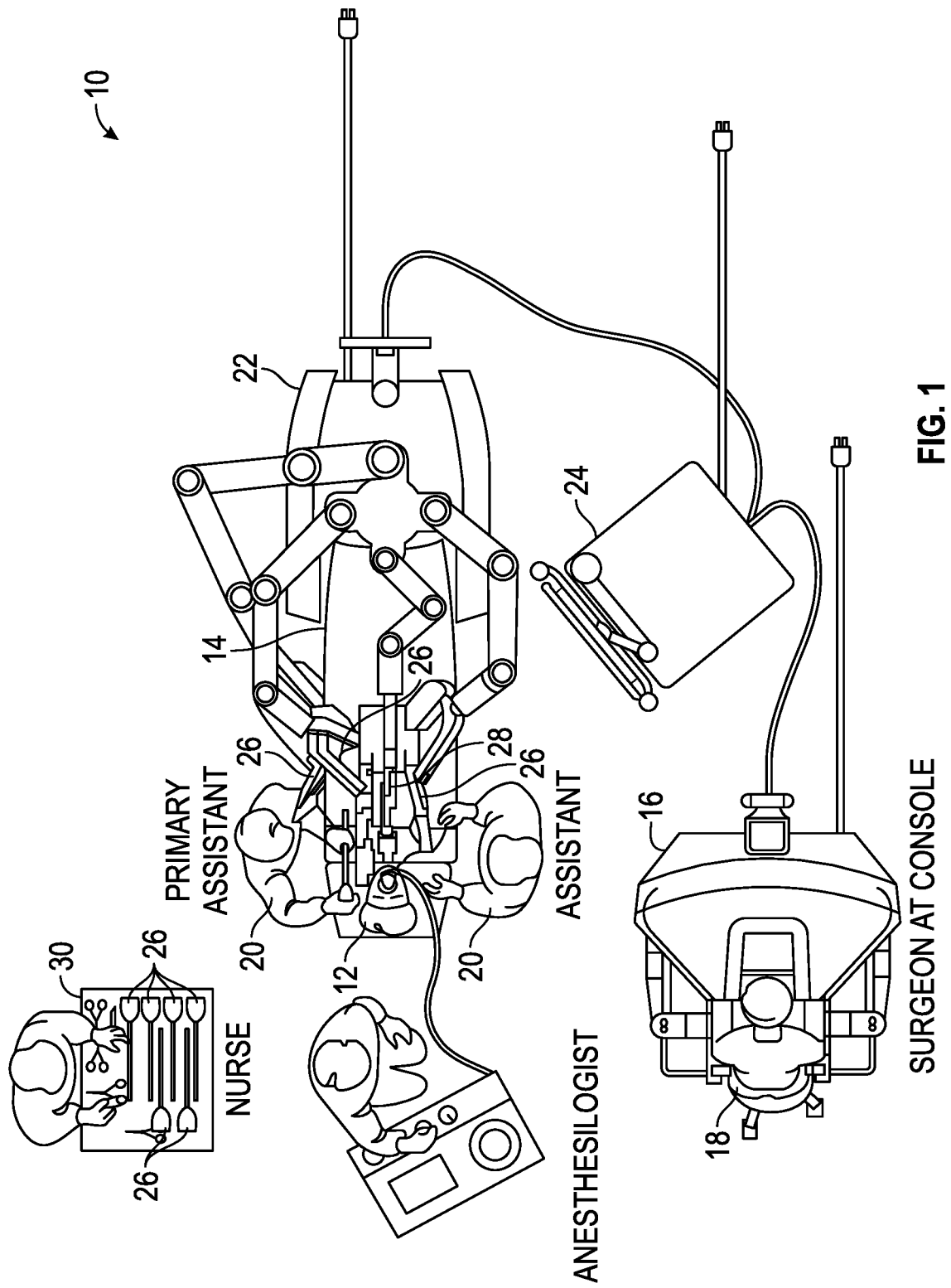
FIG. 1 is an illustrative plan view illustration of a teleoperated surgical system system in accordance with some embodiments.

1A-1B showing details of the cam drive cable flexible segment and wrist control cable segments, in accordance with some embodiments.

DESCRIPTION OF EMBODIMENTS

The following description is presented to enable any person skilled in the art to create and use a push-pull stapler with two-degree of freedom wrist for use in surgery. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Referring now to the drawings, in which like reference numerals represent like parts throughout the several views, FIG. 1 is an illustrative plan view of a teleoperated surgical system system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
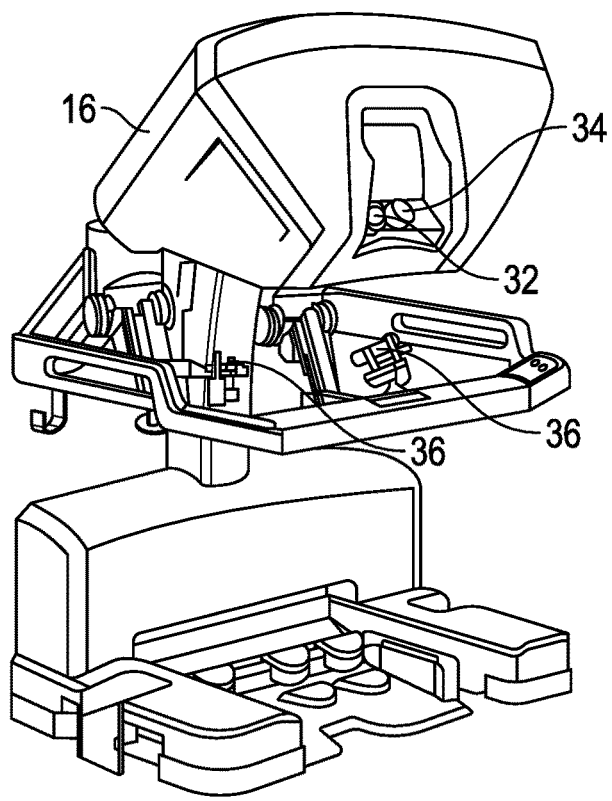
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
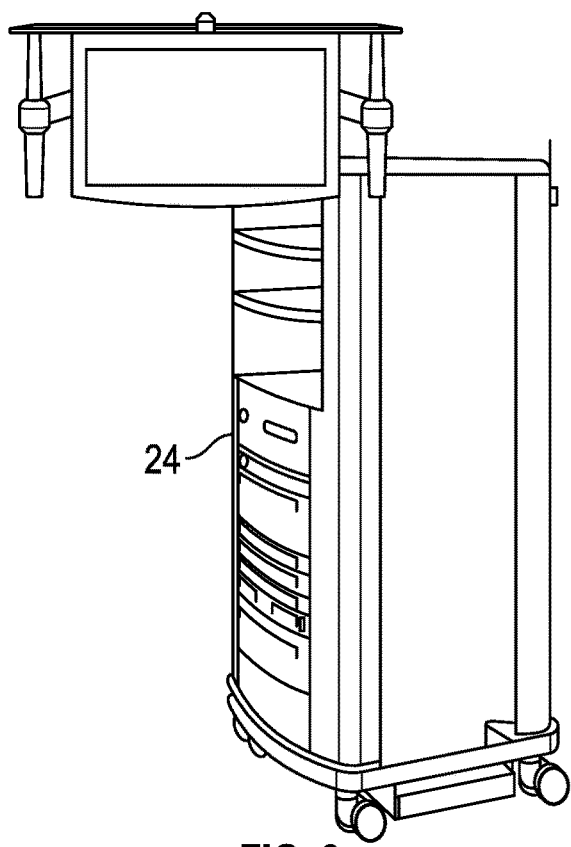
FIG. 3 is an illustrative perspective view of the Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
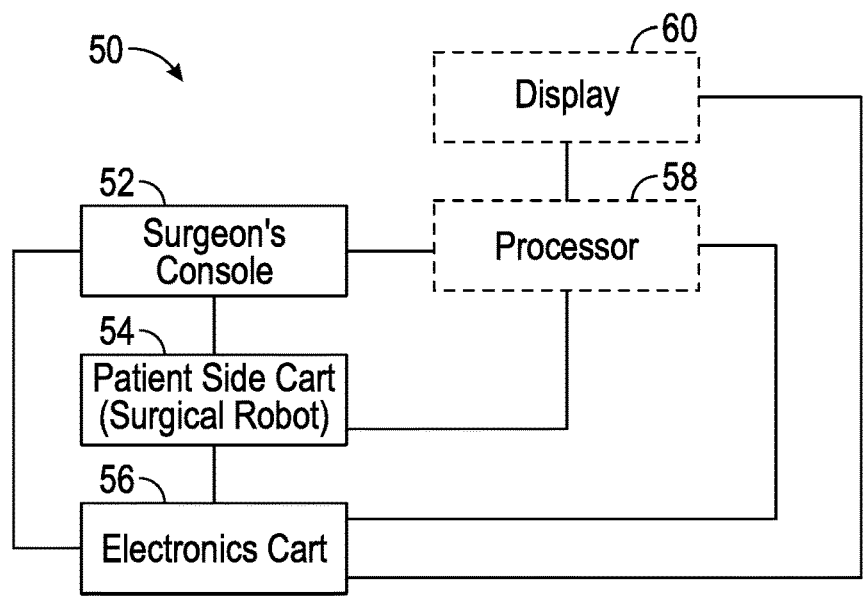
FIG. 4 is an illustrative bock diagram diagrammatically representing functional relationships among components of a teleoperated surgery system in accordance with some embodiments.

FIG. 4 is an illustrative bock diagram diagrammatically representing functional relationships among components of a teleoperated surgery system 50 (such as system system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
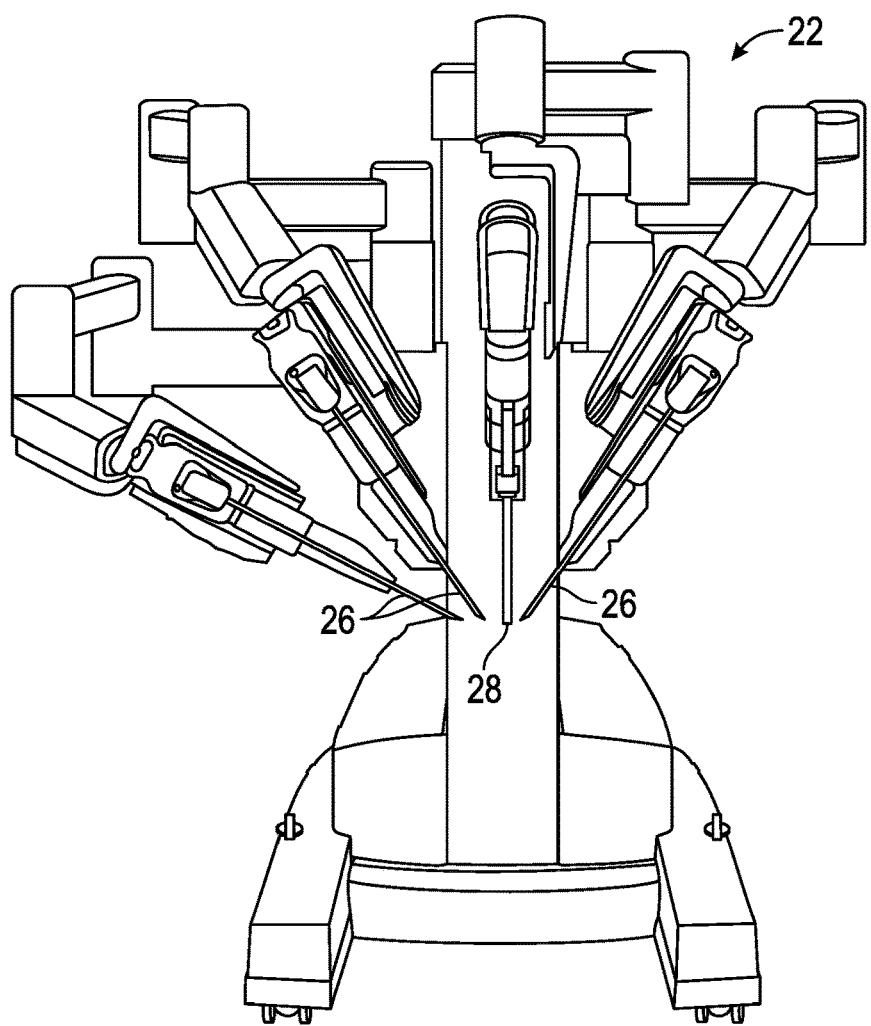
FIGS. 5A-5B are illustrative drawings showing a Patient Side Cart and a surgical tool 62, respectively in accordance with some embodiments.
Figure 5B:
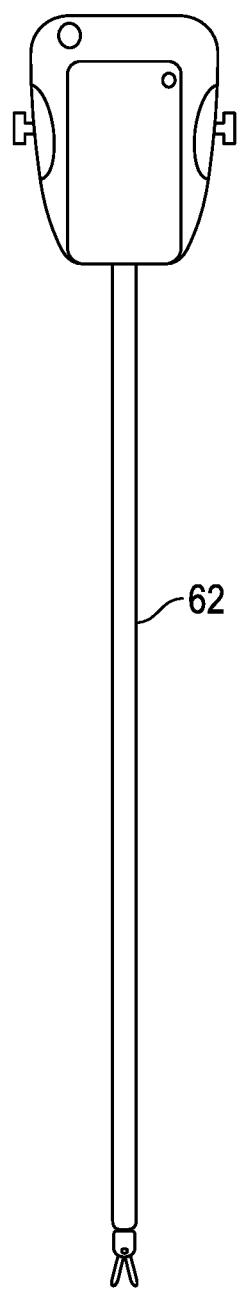

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Figure 6:
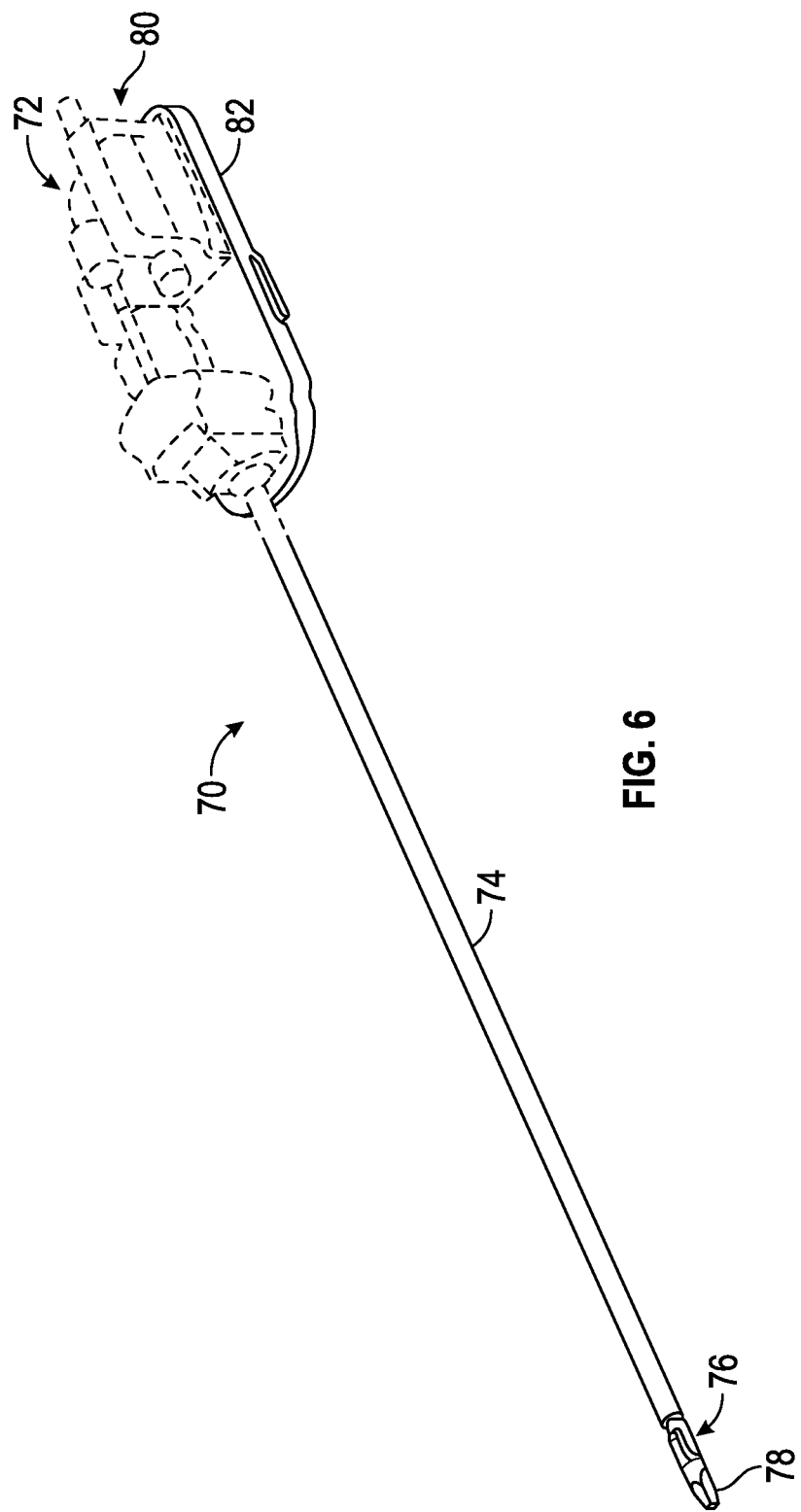
FIG. 6 is an illustrative drawing showing an example surgical tool in accordance with some embodiments.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

FIG. 7A is an illustrative partially transparent side view of a surgical tool assembly 200 with first and second jaws 214, 216 shown in a partially open position in accordance with some embodiments. FIG. 7B is an illustrative partially transparent side view of the distal portion of the surgical tool assembly of FIG. 7A, enlarged to show additional details in accordance with some embodiments. The tool assembly 200 includes a proximal actuation assembly 202, a main shaft 206, a two degree of freedom (2-dof) wrist 208, shown partially transparent using dashed lines, and an end effector 210 that includes the first and second jaws 214, 216. The end effector 210 includes an end effector base 212 coupled to a distal side of the 2-dof wrist 208, a first articulable jaw 214 and a stationary second jaw 216. The first jaw 214 has a distal end 214-1 and a proximal end 214-2. The second jaw 216 also has a distal end 216-1 and a proximal end 216-2. The end effector base 212 includes a pivot pin 217 rotatably secured to the end effector base 212 between a proximal end of the first jaw 214 and first and second lever arms 320-1, 320-2 (only one visible), about which the proximal end of the first jaw 214 and the lever arms pivots to achieve opening and closing movement of the first jaw 214 relative to the second jaw 216. In the partially open position shown in FIG. 7A, the first jaw 214 is rotated to a position in which distal ends 214-1, 216-1 of the first and second jaws 214, 216 are spaced apart sufficiently so that the jaws can be more easily maneuvered within a surgical site to encompass anatomical tissue (not shown) between them without actually clamping the tissue in place between them.

The main shaft 206 is indicated transparent using dashed lines to reveal a rigid plunger 280 that is transversely centered inside the main shaft and moveable parallel to a longitudinal axis of the main shaft 206. As explained more fully below, the plunger 280 includes an elongated plunger housing 282 operatively coupled to a distal cam drive member 344 (only a portion shown) that moves in unison with the rigid plunger 280 and passes through the wrist 208, and that in turn, is operatively connected to a cam assembly 284 used to open and close the jaws 214, 216 in response to longitudinal axial movement of the plunger 280 within the main shaft 206. In some embodiments, the drive member 344 includes a cable. Alternatively, for example, the drive member 344 includes a composite structure or a closed collided spring with a return cable, for example. Movement of the plunger 280 is controlled using one or more motors within the actuation assembly 202. In accordance with some embodiments, a first motor 281 pivotally mounted on pin 283 pushes and pulls on the plunger 280 to move it axially within the shaft 206. A second motor 285 rotates a rotational drive cable 292, described below, which rotatably drives a worm gear 293, which in turn, drives a staple pusher 244 through a staple cartridge 218.

In many embodiments, the actuation assembly 202 is operatively coupled with the wrist 208 so as to selectively reorient the end effector 210 relative to the main shaft 206 in two dimensions, referred to as pitch and yaw, and also is operatively coupled with the end effector 210 so as to actuate one or more end effector features, such as rotation of the first jaw 214 about the pivot pin 217 to open and close the first jaw 214 relative to the end effector base 212 and the second jaw 216. The wrist 208 is shown partially transparent using dashed lines to show a wrist bearing 346. In accordance with some embodiments, wrist control cables (not shown), which include flexible distal cam drive cable segments coupled with more rigid proximal hypotubes, are used to operatively couple the actuation assembly 202 with the wrist 208 so as to cause 2-dof movement of the end effector 210. As explained more fully below, the wrist control cables are routed between the actuation assembly 202 and the wrist 208 within the plunger housing 282, within the main shaft 206. The cam drive member 344 passes through the wrist bearing 346 (extension through the wrist bearing not shown), and can flex to reorient its path in response to 2-dof wrist movements. The cam drive cable, while in a flexed condition, due to 2-dof wrist movement for example, can move in unison with the plunger 280 deliver force to the cam assembly 284 to control the opening and closing of the jaws.

The cam assembly 284 includes levering-guide rollers 336-1, 336-2 that act as roller cams and corresponding levering-guide roller surfaces 332-1, 332-2 that act as levering-guide cam followers. The cam assembly 284 also includes linear-guide rollers 334-1, 334-2 that act as linear-guide cams, and corresponding linear-guide roller guide surfaces 326-1, 326-2, that act as linear-guide cam followers. The first lever arm 320-1 is shown partially transparent using dashed lines to reveal a roller guide 326-1 formed in the base 212 disposed behind it and to better reveal the linear-guide roller 334-1 that moves in contact with the linear-guide roller guide surface 326-1.

In some embodiments, the end effector 210 includes a surgical stapler. In a closed position (not shown), the first and second jaws 214, 216 are disposed parallel to each other spaced apart by an amount to accommodate anatomical tissue (not shown) that may be clamped between them. The first jaw 214 includes an anvil 220 that faces the second jaw 216. In operation, staples are disposed in a cartridge 218 (indicated by dashed lines) described below, are deformed against the anvil 220 to staple together tissue (not shown) disposed between the first and second jaws 214, 216.

Figure 8:
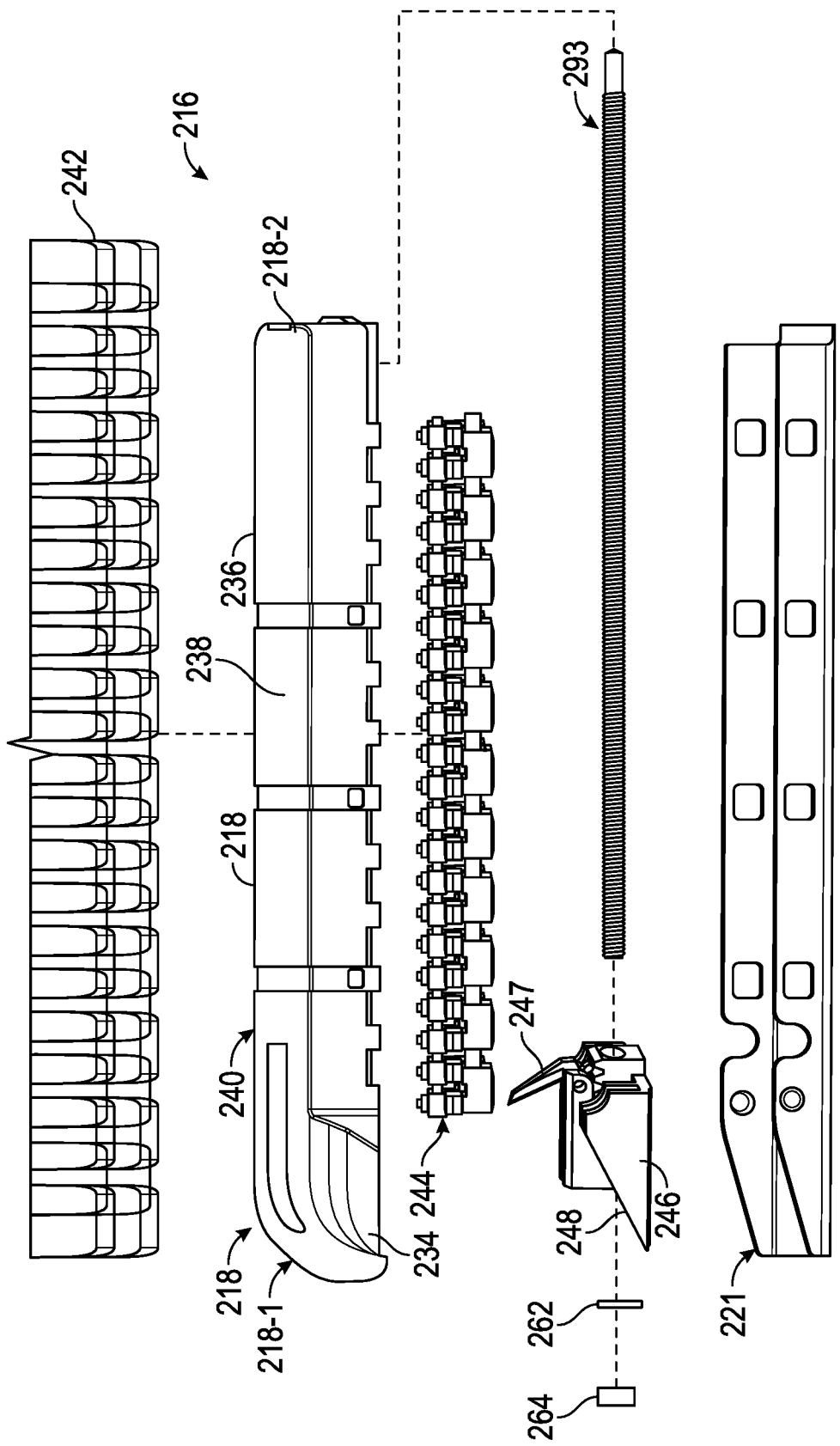
FIG. 8 is an illustrative exploded view of the second jaw in accordance with some embodiments.

FIG. 8 is an illustrative exploded view of the second jaw 216 in accordance with some embodiments. The second jaw 216 includes an elongated stapler cartridge 218 seated within a stapler cartridge support channel 221, staples 242, staple pushers 244, a drive shuttle 246, a knife 247, a lead screw 293, a thrust washer 262 and a lead screw nut 264 used to secure the lead screw. The elongated cartridge 218 includes a proximal end 218-1 and a distal end 218-2. The cartridge includes cartridge outer sidewalls 234 and an upper surface 236. The cartridge 218 carries fasteners, e.g., staples 242 to be used to attach tissue during a surgical procedure. The stapler cartridge 218 defines a central longitudinal cartridge slot 238 that extends through the cartridge 218 and extends along substantially its entire length. The stapler cartridge 218 also defines multiple laterally spaced rows of staple retention slots 240 that extend longitudinally along one side of the first cartridge slot 238 and defines multiple laterally rows of spaced staple retention slots 240 that extend longitudinally along an opposite side of the first cartridge slot 238. Each staple retention slot 240 is sized to receive a staple 242. In operation, the second jaw 216 containing a full load of staples cooperates with a surface of the anvil surface 220 facing the second jaw 216, so as to deform staples so as to fasten them to staple anatomical tissue (not shown) disposed between the jaws when they are in a closed position. Once the staples have been fired, the spent cartridge 218 can be removed and may be replaced by a replacement with a fully loaded stapler cartridge 218.

The pusher shuttle 246 includes a plurality of inclined upstanding cam wedges 248 and the knife 247 upstanding between and proximal to the cam wedges 248. The cartridge 218 defines multiple longitudinal pusher slots (not shown) in its underside along which the cam wedges 248 can slide with the knife upstanding from and sliding within the first cartridge slot 238. During operation of surgical stapler end effector 210, pusher shuttle 246 translates through the longitudinal pusher slots formed in an underside of the cartridge 218 to advance the cam wedges 248 into sequential contact with pushers 244 within the longitudinally spaced retention slots 240, to cause pushers 244 to translate vertically within retention slots 240, and to urge fasteners 242 from retention slots 240 into the staple deforming cavities (not shown) formed within the anvil 220 of the first jaw 214. As the pusher shuttle 246 translates longitudinally, it pushes up fasteners 242, which are deformed against the anvil 220. Meanwhile, the knife 247 upstands through the first cartridge slot 238 and cuts tissue between tissue regions stapled through action of the cam wedges 248, fasteners 242 and the anvil 221. U.S. Pat. No. 8,991,678 (filed Oct. 26, 2012) issued to Wellman et al., which is incorporated herein in its entirety by this reference, discloses a surgical stapler cartridge and its operation.

Figure 9:
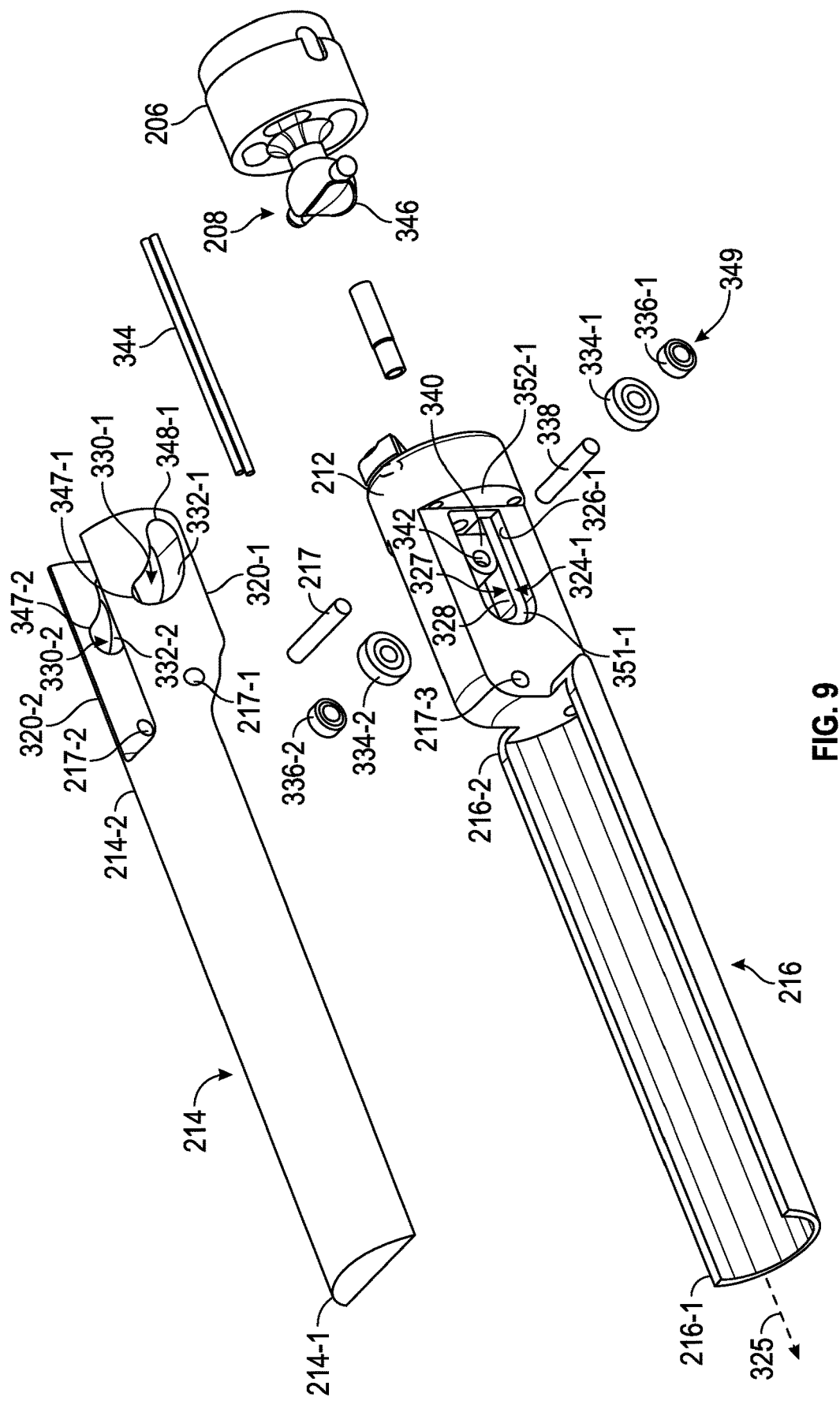
FIG. 9 is an illustrative exploded view of the first and second jaws including a cam mechanism to open and close the jaws in accordance with some embodiments.

FIG. 9 is an illustrative exploded view of a cam mechanism to open and close the jaws in accordance with some embodiments. The proximal end 214-2 of the first jaw 214 is integrally secured to opposed facing first and second lever arms 320-1, 320-2 that extend proximal to the first jaw 214. The second jaw 216 is integrally secured to the end effector base 212. The first and second first and second lever arms 320-1, 320-2 jaws define first pivot bores 217-1, 217-2 and the second jaw 216 defines a third pivot bore 217-3 that are aligned to receive a pivot axle 217 The pivot axle 217 is received in the pivot bores, 217-1, 217-2, 217-3 to rotatably mount the first jaw 214 and the first and second lever arms 320-1, 320-2 to the base 212 with the distal end 214-1 of the first jaw 214 extending distally to from the base 212 opposite the second jaw 216, and with the first and second lever arms 320-1, 320-2 extending along opposite sides of the base 212.

The base 212 defines first and second linear roller guide slots 324-1, 324-2 (only one visible.) that are aligned parallel to a longitudinal axis 325 of the second jaw 216 and that are bounded by first and second roller guide surfaces 326-1, 326-2. (only one roller guide surface visible) The base also defines a center slot 327 bounded by an surface 328 between the first and second roller guide slots 324-1, 324-2 and the first and second roller guide surfaces 326-1, 326-2. The first and second lever arms 320-1, 320-2 define first and second cam follower slots 330-1, 330-2 that are bounded by the first and second levering cam follower surfaces 332-1, 332-2. As explained more fully below, a levering force is imparted by a pair of levering-guide rollers 336-1, 336-2 to move the first jaw 214 between open and closed positions. In some embodiments the levering surfaces are covered. In an alternative embodiment, the levering cam follower surfaces 332-1, 332-2 are straight but configured at an angle to a pair of linear roller guide slots 324-1, 324-2.

A cam pin 349 includes an axle 338 that coaxially mounts a pair of linear-guide rollers 334-1, 334-2 and a pair of levering-guide rollers 336-1, 336-2. The cam pin is mounted on a bearing 342. The cam pin is disposed so that first and second linear-guide rollers 334-1, 334-2 engage the first and second linear roller guide slots 324-1, 324-2 and so that the first and second levering-guide rollers 336-1, 336-2 engage the first and second cam follower slots.

More particularly, the first and second linear roller guide slots 324-1, 324-2 each is sized to receive one of a pair of linear-guide rollers 334-1, 334-2 that are rotatably moveable to traverse its length. Similarly, the first and second cam follower slots 330-1, 330-2 each is sized to receive one of a pair of levering-guide rollers 336-1, 336-2 that are rotatably moveable to traverse its length. The pair of rollers 334-1, 334-2 and the pair of roller cams 336-1, 336-2 are rotatably mounted, coaxially, to an axle 338, which acts as a bearing for the pair of roller cams 334-1, 334-2 and for the pair of roller cams 336-1, 336-2. More particularly, the pair of roller cams 336-1, 336-2 are mounted to the axle 338 between the pair of levering-guide roller cams 336-1, 336-2. An axle bearing 340 is mounted within the center slot 327 defined by surface 328 The axle 338 is mounted within in a bore 342 formed in the axle bearing 340 to permit rotation of the linear-guide rollers 334-1, 334-2 and the levering-guide rollers 336-1, 336-2. In some embodiments, a flexible distal cam drive cable segments 344-1 extends through the wrist bearing 346 in the 2-dof wrist 208 and into the center slot 327 and acts as a linear drive to drive the axle bearing 340, in a linear motion, parallel to the second jaw axis 325 within the center slot 327. The cam drive member 344 is moveable axially, through force applied by the first motor 281, within the center slot 327 in a direction parallel to the longitudinal axis 325 of the second jaw 216. A distal end of the cam drive member 344 is secured proximal to the axle bearing 340 so that the axle bearing 342, and the linear-guide rollers 334-1, 334-2 and levering-guide roller guides 336-1, 336-2 mounted thereto, move in unison with axial movement of the cam drive member segment 344.

It will be appreciated that the axle bearing 340 acts as a cam driver since it mounts the axle 338 on which the linear-guide rollers 334-1, 334-2 and the roller cams 336-1, 336-2 are rotatably mounted, and linear motion of the axle bearing 340 within the center slot 327 drives the cam action of the roller cams 336-1, 336-2. It will be further appreciated that the roller guide surfaces 326-1, 326-2 act as cam guide surfaces that guide movement direction of the linear-guide rollers 334-1, 334-2 and the levering-guide rollers 336-1, 336-2 coaxially mounted to the axle 338. It will be further appreciated that the second jaw is integrally secured to and is an integral portion of the base and that direction of linear motion of the axle bearing within the center slot and direction of linear motion of the roller cams along the linear roller guide surfaces 326-1, 326-2 are parallel to a longitudinal axis 325 of the second jaw 216.

FIGS. 10A-10C are illustrative partially transparent upper-side perspective views of the jaws and base portions of an end effector in accordance with some embodiments in open (FIG. 10A), partially closed (FIG. 10B) and closed (FIG. 10C) positions in accordance with some embodiments. The first jaw 214 and the first lever arm 320-1 are shown partially transparent, using dashed lines, so as to reveal structures disposed behind them; the second lever arm 320-2 is not visible. Also, the second jaw 216 is shown with the cartridge 218 removed so as to simplify the drawing. FIGS. 11A-11C are enlarged partially transparent enlarged side views of the first cam follower slot 330-1 and the first levering-guide roller cam 336-1 disposed therein abutting a levering cam follower distal end edge (FIG. 11A), abutting only levering cam follower side edges (FIG. 11B) and abutting a levering cam follower proximal end edge (FIG. 11C) in accordance with some embodiments. The enlarged portion of the first lever arm 320-1 is shown partially transparent, using dashed lines, so as to reveal structures disposed behind it.

Referring collectively to FIG. 9 and to FIGS. 10A-10C and to FIGS. 11A-11C, in operation, the cam drive member 344 drives the pair of levering-guide rollers 336-1, 336-2 (only the first roller cam visible) parallel to the longitudinal axis 325 of the second jaw 216.

The cable drive 344 imparts a linear motion to the bearing 340, which imparts a linear motion to the linear-guide rollers 334-1, 334-2 within the linear roller guide slots 324-1, 324-2 bounded by the first and second linear roller guide surfaces 326-1, 326-1. The levering-guide rollers 336-1, 336-2 coaxially mounted to axle 338 move in a linear direction in unison with the roller cams 334-1, 334-2 within levering roller guide slots 330-1, 330-2 bounded by the first and second levering roller guide surfaces 332-1, 332-2. Interaction of the linear-guide rollers 334-1, 334-2 with the first and second levering roller guide surfaces 332-1, 332-2 imparts lever force to lever arms 320-1, 320-2 that causes a rotation motion of the about the pivot 217 that moves the first jaw 214 in a direction opposite to the direction of the lever force.

The first and second levering roller guides 332-1, 332-2 each includes a respective distal portion 347-1, 347-2 and respective proximal portion 348-1, 348-2. The distal portion 347-1, 347-2 of each levering roller guide 332-1, 332-2 is disposed relative to the pivot 217 so that interaction between the levering-guide roller cams 336-1, 336-2 and the distal portions 347-1, 347-2 of the levering roller guides 332-1, 332-2 imparts a lever force to cause the first jaw 214 to rotate in a direction toward the second jaw 216 so as to close the jaws. The proximal portions 348-1, 348-2 of each levering roller guide 332-1, 332-2 is disposed relative to the pivot 217 so that interaction between the roller cams 336-1, 336-2 and the proximal portions 348-1, 348-2 of the levering roller guides 332-1, 332-2 imparts a lever force to cause the first jaw 214 to rotate in a direction away from the second jaw 216 so as to open the jaws.

The base 212 defines the first and second elongated linear roller guide slots 324-1, 324-2 each sized to receive one of the pair of linear-guide rollers 334-1, 334-2. The first and second linear roller guide slots 324-1, 324-2 constrain the first and second roller guides 334-1, 334-2 to movement parallel to the longitudinal axis 325 of the second jaw 216. The first and second roller linear-guide rollers 334-1, 334-2 are mounted coaxially with the first and second rollers 336-1, 336-2 so as to guide the levering-guide rollers 336-1, 336-2 in a linear motion parallel to the longitudinal axis 325 of the second jaw 216 while the levering-guide rollers 336-1, 336-2 interact with the pair of levering roller guides 332-1, 332-2 to impart rotation motion to the first jaw 314 about the pivot 217.

More specifically, the first and second linear roller guide slots 324-1, 324-2 are aligned parallel to the longitudinal axis 325 of the second jaw 216 and are bounded by first and second linear roller guide surfaces 326-1,326-2. The first and second linear guide slots 324-1, 324-2 are disposed on opposed sides of the base 212 and are aligned with each other. The first and second linear roller guide surfaces 326-1, 326-2 each include a respective distal end portion 351-1 and a respective proximal end portion 352-1. The first and second linear roller guide surfaces 326-1, 326-2 each includes a corresponding pair of opposed roller guide side edges uniformly spaced apart from each other along their lengths to constrain movement of a linear-guide roller guide roller 334-1, 334-2 received between them to a linear path that is parallel to the longitudinal axis 325 of the second jaw 216 and that extends between its distal end portion 351-1, 351-2 and its proximal end portion 352-1, 352-2. The linear roller guide surface distal end portions 351-1, 351-2 define respective distal stop surfaces to constrain distal-direction movement of the roller cams 334-1, 334-2. Additionally, the linear roller guide surface proximal end portions 352-1, 352-2 define respective proximal stop surfaces to constrain proximal direction movement of the roller cams 334-1, 334-2.

Each of the first and second roller levering roller guide surfaces 332-1, 332-2 includes a respective pair of opposed cam follower side edges uniformly spaced apart from each other along their lengths the between the roller cam follower distal end portions 347-1, 347-2 and the roller cam follower proximal end portions 348-1, 348-2. The levering roller cam surface distal end portions 347-1, 347-2 define respective distal stop surfaces to constrain distal-direction movement of the levering-guide roller cams 336-1, 336-2. Additionally, the levering roller cam surface proximal end portions 348-1, 348-2 define respective proximal stop surfaces to constrain proximal direction movement of the levering-guide roller cams 336-1, 336-2.

As explained above, in operation, the first and second linear roller guide surfaces 326-1, 326-2 constrain both the linear-guide roller guides 334-1, 334-1 and the roller cams 336-1, 336-2 to follow a path parallel to the axis 325 of the second jaw 216. The first and second levering roller guide surfaces 332-1, 332-2 formed in the base 212 are inclined relative to the first and second linear roller guide surfaces 326-1, 326-2 formed in the first and second lever arms 320-1, 320-2 such that during linear motion of the linear-guide rollers 334-1, 334-2 and the roller cams 336-1, 336-2 parallel to the axis 325, the first and second roller levering cams surfaces 336-1, 336-2 impart a lever force to the first and second levering-guide rollers 336-1, 336-2 causing rotation of the first arm 214 and of the first and second lever arms 320-1, 320-2 about the pivot axis 217.

Moreover, the first and second levering roller guide surfaces 332-1, 332-2 are contoured so as to amplify the lever force imparted by the roller cams 336-1, 336-2 when they are disposed in either the distal end portions 347-1, 347-2 or the proximal end portions 348-1, 348-2 of the first and second levering roller guide surfaces 332-1, 332-2. More specifically, in accordance with some embodiments, the first and second levering roller guide slots 330-1, 330-2 and the opposed levering roller guide surface side edges 332-1, 332-2 have a curved contour to steer the levering-guide rollers 336-1, 336-2 to and from the levering roller guide surface' distal end portions 347-1, 347-2 and to and from the levering roller guide surfaces' proximal end portions 348-1, 348-2.

As best shown in FIG. 10B and FIG. 11B, during passage of the roller cams 336-1, 336-2 within portions of the first and second levering roller guide surfaces 332-1, 332-2 that are between the proximal and distal end portions, the roller cams 336-1, 336-2 interact with the roller levering roller guide surfaces 332-1, 332-2 to impart rotation motion to the lever arms 320-1, 320-2 and to the first arm 214. As best shown in FIG. 10A and FIG. 10A, when the roller cams 336-1, 336-2 abut the levering roller guide surfaces' distal edges 347-1, 347-2, no further rotation of the lever arms 320-1, 320-2 and the first arm 214 is possible since the roller cams have reached the distal ends 347-1, 347-2 of the levering roller guide surfaces 332-1, 332-2. Consequently, the levering-guide rollers 336-1, 336-2 transfer to the levering roller guide surface distal edges 347-1, 347-2 a lever force that matches the distal direction force applied by the cam drive member 344 to the axle bearing 342, resulting in the exerting of a maximal jaw opening rotation force to the first jaw 214. Conversely, as best shown in FIG. 10C and FIG. 11C, when the levering-guide rollers 336-1, 336-2 abut the levering roller guide surface proximal edges 348-1, 348-2, no further rotation of the lever arms 320-1, 320-2 and the first arm 214 is possible since the roller cams have reached the proximal ends 348-1, 348-2 of the levering roller guide surfaces 332-1, 332-2. Consequently, the levering-guide roller cams 336-1, 336-2 transfer to the cam follower proximal edges 348-1, 348-2 a lever force that matches the proximal direction force applied by the cam drive member 344 to the axle bearing 342, resulting in the exerting of a maximal jaw closing rotation force to the first jaw 214.

Figure 12:
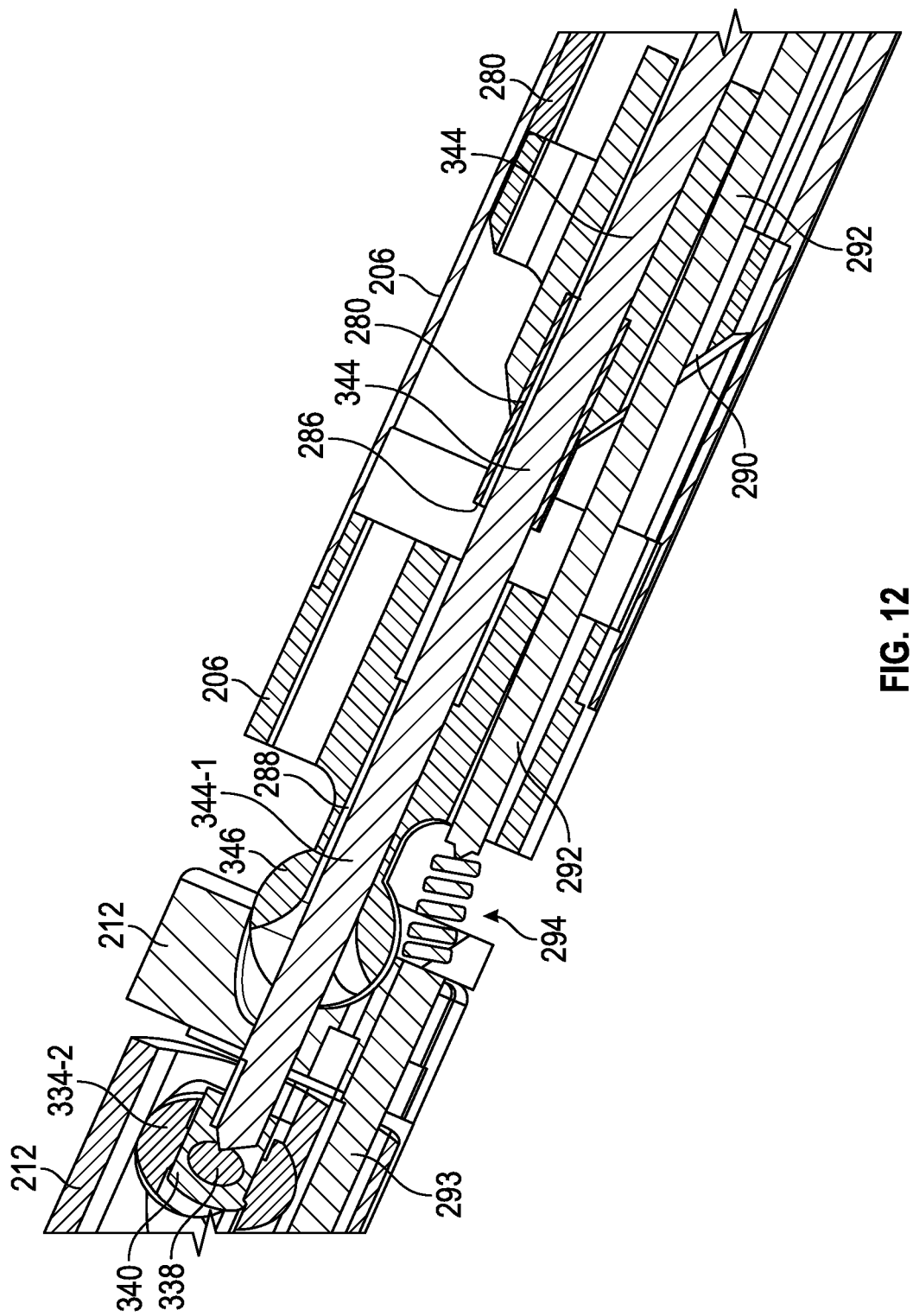
FIG. 12 is an illustrative cross-sectional view of a portion of the surgical tool assembly of FIGS. 7A-7B showing details of the cam drive cable flexible segment traversing the wrist and also showing a staple driver drive cable segment traversing the wrist, in accordance with some embodiments.

FIG. 12 is an illustrative cross-sectional view of a portion of the surgical tool assembly of FIGS. 7A-7B showing details of the cam drive member 344 traversing the wrist 208 and also showing a staple driver drive cable 902 traversing the wrist 208 in accordance with some embodiments. In accordance with some embodiments, the plunger 280 defines a centrally disposed cam drive cable passage 286 in which the cam drive member 344 is attached so that the cam drive member 344 moves in unison with axial movement of the plunger 280 within the main shaft 206. The center passage 286 defined by the plunger is aligned with a center passage 288 defined through the wrist bearing 346 through which the flexible cam drive 344 passes and moves freely in unison with axial movement of the plunger 280 within the main shaft 206. The cam drive member 344 extends distally from the wrist bearing and is secured to a proximal side of to the axle bearing 340, which moves in unison with it as explained above.

In accordance with some embodiments, the plunger 280 also defines a staple drive cable passage 290 in which a rotatable flexible rotational drive cable 292 extends between the proximal actuation assembly 202 and a lead screw 293. The flexible staple drive cable 292 and the lead screw 293 are axially secured so that they rotate in unison; rotation imparted by the second motor 285 to the rotational drive cable 292 is imparted to lead screw 293. The lead screw 293 engages with a complementary threaded surface of the staple pusher 244 such that that rotation of the lead screw 293 results in linear motion of the staple pusher 244 in a distal direction along the second jaw axis 325 whereby staples are driven for deformation against the anvil 221 as described above. U.S. Pat. No. 8,991,678, which has been incorporated by reference, describes use of a screw drive to drive a staple pusher. In some embodiments, the staple drive cable 292 includes a rotational torque coil (sometimes referred to as a 'speedo cable') to impart a rotational force to the lead screw, which also permits two-degree of freedom flexing of the rotational drive cable 292 in a region 294 where it traverses the wrist 208 portion. Alternatively, for example, the staple drive cable 292 can include a wound up coil such as a closed coiled spring that is configured to provide toque when rotated. Alternatively, a two-degree of freedom flexible coupling member (not shown) such as a cardan, a flexible drive shaft, a U-joint, a double U-joint, or snake-style linkages secures the rotational drive cable 292 to the lead screw 293 in the region 294, to permit two-degree of freedom flexing, while the rotational drive cable 292 imparts an off-axis rotation force to the lead screw 293, for example.

Figure 13:
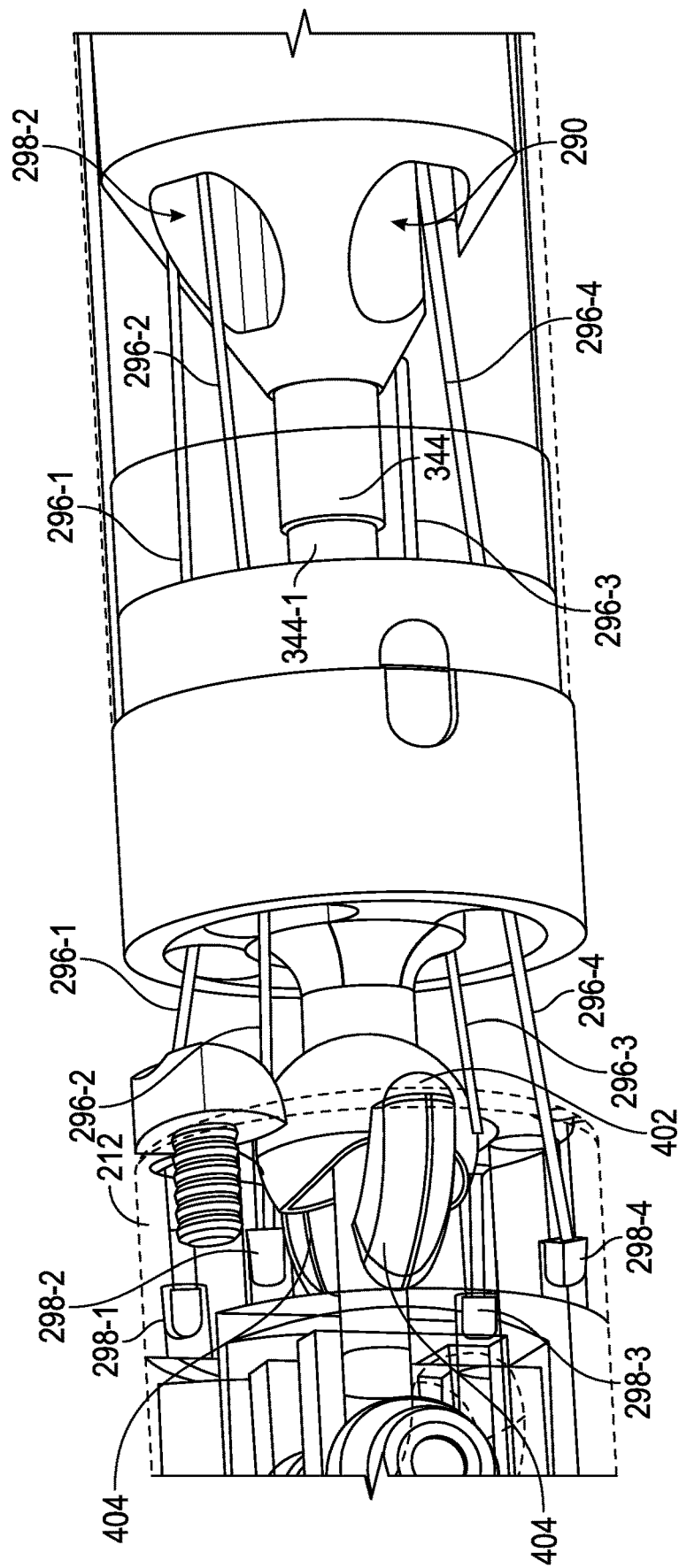
FIG. 13 is an illustrative partially transparent perspective view of a portion of the surgical tool assembly of FIGS.

FIG. 13 is an illustrative partially transparent perspective view of a portion of the surgical tool assembly of FIGS. 7A-7B showing details of the flexible cam drive member 344 traversing the wrist 208 in accordance with some embodiments. The wrist includes a ball joint bearing 346 that depends from a distal end of the shaft 206. Coupling pins 402 rotatably mount the base portion 212 of the end effector 210 to the bearing 346 for motion in two degrees of freedom (2-dof). More specifically, wrist coupling pin 402 rotatably mounts the bearing 346 to the base 212 so as to permit rotation of the end effector 210 in a first degree of freedom relative to the bearing 346. Moreover, the base 212 defines transverse slots 404 that permit rotation of the end effector 210 in a second degree of freedom relative to the bearing 346. Wrist control cable segments 296-1 to 296-4 extend through the main shaft 206 and the plunger 280 secured within wrist 208 to control wrist movement, in accordance with some embodiments. The main shaft 206 and the base 212 are shown partially transparent using dashed lines to show structures within them. The wrist control cable segments 296-1 to 296-4 extend into the wrist 208 to attachments 298-1 to 298-4 used to secure them to the wrist 208. The end effector 210, which includes the first and second jaws 214, 216 is moveable in two degrees of freedom (2-dof) in response to selective tension and corresponding relaxation forces provided to the wrist control cables. The plunger 280 defines passages 298-1, 298-2 (only one visible) to permit passage of first and second wrist cables 296-1, 296-2. The passage 290 is sized large enough to allow passage of third and fourth wrist cables 296-3, 296-4 in addition to the rotational drive cable 292. U.S. Pat. No. 8,852,174 (filed Nov. 12, 2010) issued to Burbank, which is incorporated herein in its entirety by this reference, discloses prior surgical tools that include two degree of freedom wrists.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A surgical instrument comprising:
a first jaw having a distal end and a proximal end wherein the proximal end of the first jaw is attached to a lever arm that includes a levering cam slot having a proximal portion and a distal portion;
a second jaw having a distal end and a proximal end wherein the proximal end of the second jaw is secured to a base that includes a linear cam slot aligned with a longitudinal axis of the second jaw axis and having a proximal portion and a distal portion;
a pivot rotatably mounting the first jaw to the second jaw, wherein a pivot axis extends between the first jaw and the lever arm;
a cam pin configured to extend through and engage the levering cam slot and the linear cam slot;
a shaft that includes a proximal end portion and a distal end portion;
a two degree of freedom wrist that includes a ball joint bearing that extends from the distal end portion of the shaft, the bearing defining a passage through the bearing; and
a flexible cam drive member that passes within the passage through the bearing, and that can flex to reorient a path of the flexible cam drive member in response to two degree of freedom wrist movement, and that is operatively coupled to drive the cam pin to follow the linear cam slot;
wherein the distal portion of the levering cam slot is disposed such that the cam pin imparts a lever force upon the lever arm that rotates the first jaw away from the second jaw when the cam pin contacts the distal portion of the levering cam slot and wherein the proximal portion of the levering cam slot is disposed such that the cam pin imparts a lever force upon the lever arm that rotates the first jaw toward the second jaw when the cam pin contacts the proximal end portion of the levering cam slot.

2. The surgical instrument of claim 1,
wherein the cam pin includes a levering-guide cam disposed to follow the levering cam slot and includes a linear-guide cam disposed to follow the linear cam slot and the levering-guide cam and the linear guide cam are operatively coupled to move in unison.

3. The surgical instrument of claim 1,
wherein the first jaw levering cam slot has a curved contour.

4. The surgical instrument of claim 1,
wherein the levering cam slot has a linear contour.

5. The surgical instrument of claim 1,
wherein the cam pin includes a levering-guide roller cam disposed to follow the levering cam slot and includes a linear-guide roller cam disposed to follow the linear cam slot; and
wherein the levering-guide roller cam and the linear-guide roller cam are operatively coupled to move in unison.

6. The surgical instrument of claim 1,
wherein the cam pin includes a levering-guide roller cam disposed to follow the levering cam slot and includes a linear-guide roller cam disposed to follow the linear cam slot; and
wherein the cam pin includes an axle coaxially mounting the levering-guide roller and the linear-guide roller; and
wherein the flexible cam drive member is disposed to impart a linear motion to the axle, to drive the linear-guide roller mounted thereon, in contact with the second jaw linear guide surface, in a direction parallel to the longitudinal axis of the second jaw.

7. The surgical instrument of claim 1,
wherein the cam pin includes a levering-guide roller cam disposed to follow the levering cam slot and includes a linear-guide roller cam disposed to follow the linear cam slot; and
wherein the cam pin includes an axle coaxially mounting the levering-guide roller and the linear-guide roller; and
wherein the flexible cam member is disposed to impart a linear motion to the axle, to drive the linear-guide roller mounted thereon, in contact with the linear guide surface, in a direction parallel to the longitudinal axis of the second jaw; and
wherein the flexible cam member is disposed to impart a linear motion to the axle,
to drive the linear-guide roller mounted thereon within the second jaw linear guide slot in a direction parallel to the longitudinal axis of the second jaw, and
to drive the levering-guide roller mounted thereon within the levering-guide slots between the proximal portion of the levering cam slot levering-guide and the distal portion of the levering cam slot levering-guide.

8. The surgical instrument of claim 1 further including:
a motor to move the flexible cam drive cable longitudinally within the shaft.

9. The surgical instrument of claim 1 further including:
a staple cartridge disposed within the second jaw;
a drive shuttle;
a screw drive to drive the drive shuttle within the cartridge in a direction parallel to a longitudinal axis of the second jaw; and
a rotational drive extending within the shaft between the proximal end portion of the shaft and the distal end portion of the shaft, including a flexible region that traverses the wrist, operatively coupled to impart a rotational force to the screw drive that can flex to permit two-degree of freedom flexing of the rotational drive while the rotational drive cable imparts an off-axis rotation force to the lead screw drive.

10. The surgical instrument of claim 9,
the rotational drive including a rotational drive cable that extends within the shaft between the proximal end portion of the shaft and the distal end portion of the shaft; and further including:
a two degree of freedom coupling member operatively coupled between the rotational drive cable and the screw drive.

11. A surgical instrument comprising:
a first jaw having a distal end and a proximal end wherein the proximal end of the first jaw is attached to a lever arm that includes first and second levering cam slots, each having a proximal portion and a distal portion;
a second jaw having a distal end and a proximal end wherein the proximal end of the second jaw is secured to a base that includes first and second linear cam slots, each aligned with a longitudinal axis of the second jaw axis and having a proximal portion and a distal portion;
a pivot rotatably mounting the first jaw to the second jaw, wherein a pivot axis extends between the first jaw and the lever arm;
first and second levering-guide roller cams configured to respectively extend through and engage the first and second levering cam slots;
first and second linear-guide roller cams, that are coaxially mounted with the first and second levering-guide roller cams and that are configured to respectively extend through and engage the first and second linear cam slots;
a shaft that includes a proximal end portion and a distal end portion;
a two degree of freedom wrist that includes a ball joint bearing that extends from the distal end portion of the shaft, the bearing defining a passage through the bearing;
a flexible cam drive member that passes within the passage through the bearing, and that can flex to reorient a path of the flexible cam drive member in response to two degree of freedom wrist movement, and that is operatively coupled to drive the first and second linear-guide roller cams follow the first and second linear cam slots in parallel with the longitudinal axis of the second jaw;
wherein the distal portions of the first and second levering cam slots are disposed such that the levering-guide roller cams impart a lever force upon the lever arm that rotates the first jaw away from the second jaw when the levering-guide roller cams contact the distal portions of the first and second levering cam slots and wherein the proximal portions of the first and second levering cam slots are disposed such that the levering-guide roller cams impart a lever force upon the lever arm that rotates the first jaw toward the second jaw when the levering-guide roller cams contact the proximal end portions of the first and second levering cam slots
further including:
a staple cartridge disposed within the second jaw;
a drive shuttle;
a screw drive to drive the drive shuttle within the cartridge in a direction parallel to a longitudinal axis of the second jaw; and a rotational drive extending within the shaft between the proximal end portion of the shaft and the distal end portion of the shaft, including a flexible region that traverses the wrist, operatively coupled to impart a rotational force to the screw drive that can flex to permit two-degree of freedom flexing of the rotational drive while the rotational drive cable imparts an off-axis rotation force to the lead screw drive.

12. The surgical instrument of claim 11
the bearing including a ball joint bearing.

13. The surgical instrument of claim 11
the rotational drive including rotational drive cable that extends within the shaft between the proximal portion of the shaft and the distal portion of the shaft; further including:
a two degree of freedom coupling member operatively coupled between the rotational drive cable and the screw drive.

14. The surgical instrument of claim 1,
the wrist further including at least one coupling pin rotatably mounting the bearing to the base to permit rotation of the end effector in a first degree of freedom relative to the bearing and including at least one transverse slot to receive the at least one coupling pin to permit rotation of the end effector in a second degree of freedom relative to the bearing.

15. The surgical instrument of claim 1 further including:
a rigid plunger transversely centered inside the shaft and moveable parallel to the longitudinal axis of the shaft; and
the flexible cam drive member operatively coupled to the plunger to move in unison with the plunger to deliver force to control opening and closing of the jaws.

16. The surgical instrument of claim 11,
the wrist further including at least one coupling pin rotatably mounting the bearing to the base to permit rotation of the end effector in a first degree of freedom relative to the bearing and including at least one transverse slot to receive the at least one coupling pin to permit rotation of the end effector in a second degree of freedom relative to the bearing.

17. The surgical instrument of claim 11 further including:
a rigid plunger transversely centered inside the shaft and moveable parallel to the longitudinal axis of the shaft; and
the flexible cam drive member operatively coupled to the plunger to move in unison with the plunger to deliver force to control opening and closing of the jaws.

* * * * *

UNITED STATES PATENT AND TRADEMARK OFFICE
CERTIFICATE OF CORRECTION

Page 1 of 1

PATENT NO. : 10,898,189 B2
APPLICATION NO. : 15/772530
DATED : January 26, 2021
INVENTOR(S) : William A. McDonald, II It is certified that error appears in the above-identified patent and that said Letters Patent is hereby corrected as shown below:

On the Title Page

On page 2, in Column 1, under "Abstract", Line 4, delete "way" and insert --away-- therefor Signed and Sealed this
Twenty-third Day of March, 2021

Drew Hirshfeld
*Performing the Functions and Duties of the
Under Secretary of Commerce for Intellectual Property and
Director of the United States Patent and Trademark Office*